(12) United States Patent
Foley

(10) Patent No.: US 8,544,660 B2
(45) Date of Patent: Oct. 1, 2013

(54) RACK FOR SURGICAL SPONGE COUNTER BAGS THAT FACILITATES SPONGE COUNTING

(76) Inventor: Frances P. Foley, Worcester, MA (US)

( * ) Notice: Subject to any disclaimer, the term of this patent is extended or adjusted under 35 U.S.C. 154(b) by 34 days.

(21) Appl. No.: 13/149,700

(22) Filed: May 31, 2011

(65) Prior Publication Data

US 2012/0132600 A1 May 31, 2012

Related U.S. Application Data

(60) Provisional application No. 61/353,283, filed on Jun. 10, 2010.

(51) Int. Cl.
*A47G 29/00* (2006.01)

(52) U.S. Cl.
USPC .......... 211/85.15; 211/168; 177/15; 177/245; 206/370

(58) Field of Classification Search
USPC ................... 211/119.004, 113, 119.009, 168, 211/85.15, 78, 163, 95, 96, 115, 116; 206/370, 206/362, 438; 340/10.5, 5.92, 568.1; 235/492; 604/362, 317; 248/95, 98; 177/15, 245
See application file for complete search history.

(56) References Cited

U.S. PATENT DOCUMENTS

| | | | | | |
|---|---|---|---|---|---|
| 1,435,110 | A | * | 11/1922 | Efford | 211/96 |
| 1,818,761 | A | * | 8/1931 | Sendler | 211/1.3 |
| 2,561,806 | A | * | 7/1951 | Mailland | 211/96 |
| 2,987,193 | A | * | 6/1961 | Pajor | 211/89.01 |
| 3,749,237 | A | * | 7/1973 | Dorton | 206/438 |
| 4,295,537 | A | * | 10/1981 | McAvinn et al. | 177/15 |
| 4,428,488 | A | * | 1/1984 | McAvinn et al. | 211/181.1 |
| 5,582,301 | A | * | 12/1996 | Josephson | 211/85.1 |
| 6,070,747 | A | * | 6/2000 | Shea | 211/87.01 |
| 6,196,398 | B1 | * | 3/2001 | Lowe | 211/96 |
| 6,607,170 | B1 | * | 8/2003 | Hoftman | 248/129 |

* cited by examiner

*Primary Examiner* — Korie H Chan
(74) *Attorney, Agent, or Firm* — Blodgett & Blodgett, P.C.; Gerry A. Blodgett; David J. Blodgett

(57) ABSTRACT

A rack for surgical sponge counter bags that facilitates sponge counting, comprising a spindle and a plurality of rotatable support members mounted for rotation about the spindle, each support member carrying one or more mechanical devices that are constructed and adapted to grasp a sponge counter bag.

2 Claims, 2 Drawing Sheets

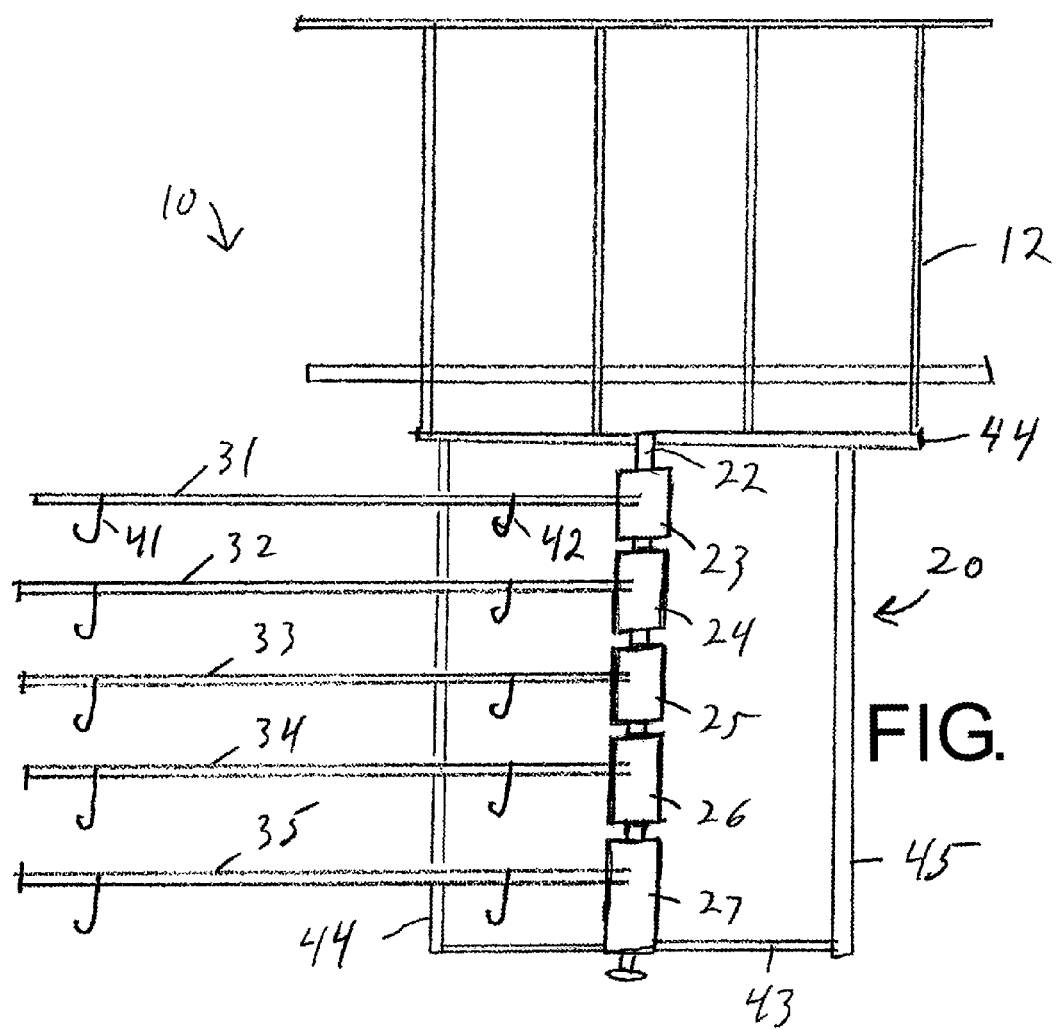

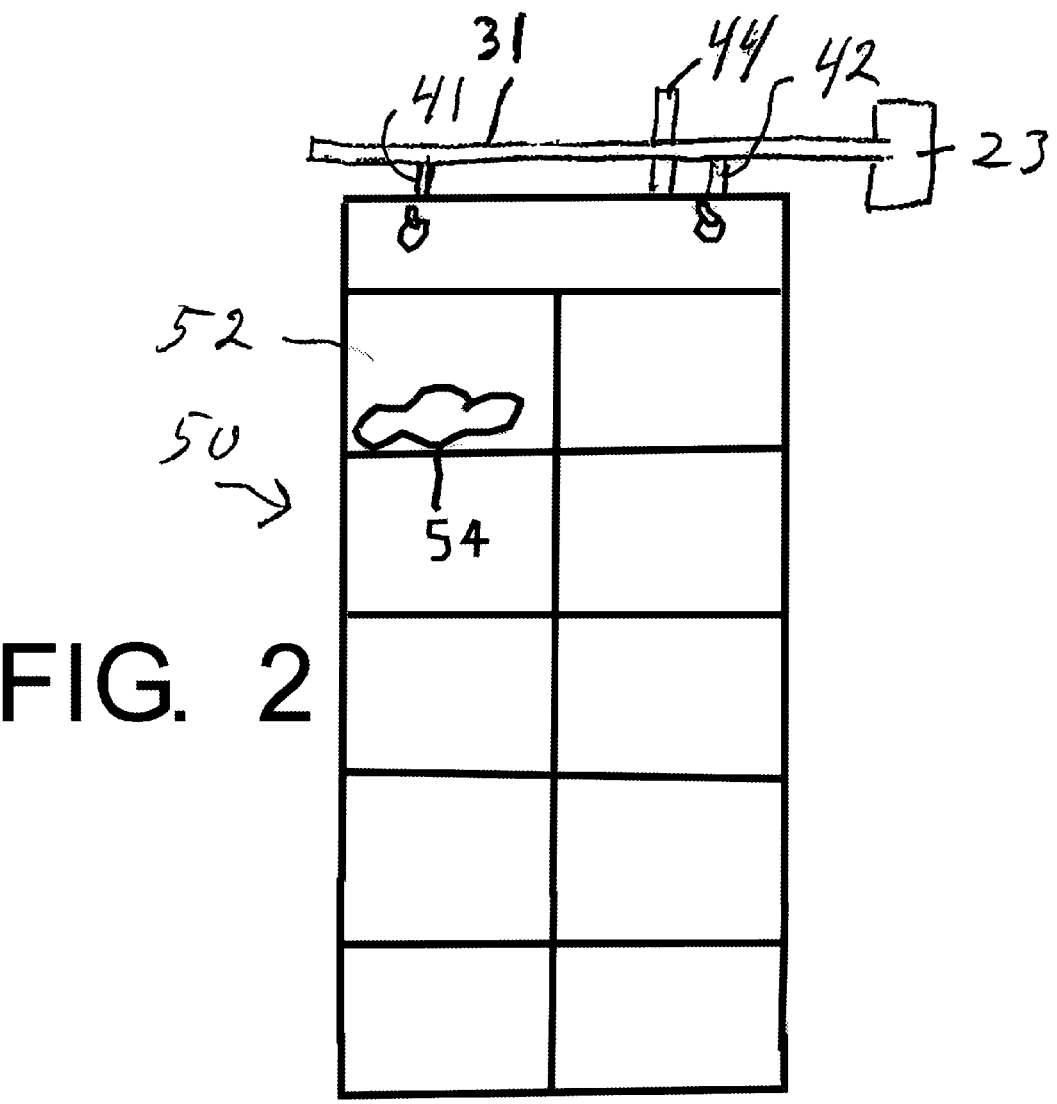

RACK FOR SURGICAL SPONGE COUNTER BAGS THAT FACILITATES SPONGE COUNTING

CROSS-REFERENCE TO RELATED APPLICATIONS

This application claims the benefit under 35 U.S.C. section 119(e) of U.S. Provisional patent application No. 61/353,283 filed Jun. 10, 2010, all of which is hereby incorporated by reference.

STATEMENT REGARDING FEDERALLY SPONSORED RESEARCH OR DEVELOPMENT

This invention has been created without the sponsorship or funding of any federally sponsored research or development program.

REFERENCE TO SEQUENCE LISTING, A TABLE, OR A COMPUTER PROGRAM LISTING COMPACT DISK APPENDIX

Not applicable.

THE FIELD OF THE INVENTION

This invention involves a rack for surgical sponge counter bags.

BACKGROUND OF THE INVENTION

In the conduct of surgical procedures, it is essential that all of the sponges and similar items, used in the procedure, are accounted for before the procedure is completed. However, because of the very difficult conditions that often exist during the procedure, the current accounting systems are not always effective.

These and other difficulties experienced with the prior art devices have been obviated in a novel manner by the present invention.

It is, therefore, an outstanding object of some embodiments of the present invention to provide a rack for surgical sponge counter bags that provides an simple, efficient, and very reliable method for accounting for the surgical sponges, and surgical squares.

With these and other objects in view, as will be apparent to those skilled in the art, the invention resides in the combination of parts set forth in the specification and covered by the claims appended hereto, it being understood that changes in the precise embodiment of the invention herein disclosed may be made within the scope of what is claimed without departing from the spirit of the invention.

BRIEF SUMMARY OF THE INVENTION

This invention involves a rack for surgical sponge counter bags that facilitates sponge counting, comprising a spindle and a plurality of rotatable support members mounted for rotation about the spindle, each support member carrying one or more mechanical devices that are constructed and adapted to grasp a sponge counter bag. The system also has a stop to keep the support members from rotating all of the way around the spindle.

BRIEF DESCRIPTION OF THE SEVERAL VIEWS OF THE DRAWING

The character of the invention, however, may best be understood by reference to one of its structural forms, as illustrated by the accompanying drawings, in which:

FIG. 1 is diagrammatic view of a sponge bag rack embodying the principles of the present invention, and, FIG. 2 is a diagrammatic view of a sponge bag rack embodying the principles of the present invention.

DETAILED DESCRIPTION OF THE INVENTION

Referring first to FIG. 1 and which are shown the general features of one embodiment of the present invention, the invention involves a rack that is constructed to hold a number of surgical sponge counter bags, such as the "CountEZ Sponge Counter Bags" from Xodus Medical. The bags have a number of separate pockets. The contents are visible through the clear front panel. Sponges and/or lap pads (squares) are placed into the pockets. The visibility assists with keeping a count of the sponges and/or lap pads (squares).

A problem is that in many surgeries, multiple bags are used. It thus becomes necessary for the personnel to keep track of and count the bags, as well as the sponges in the bags. There is thus the need for a system that facilitates handling multiple such bags.

The invention comprises a rack that has a number of bag supports. Each such support is designed to hold one bag. The supports are rotatable about a spindle with a stop to prevent the supports from rotating completely around the spindle. The stop thereby prevents double counting. The rack facilitates counting of sponges, as, after the sponges in each bag are counted, the support can be rotated half way about the spindle to expose the next bag. The support can only rotated half way around the spindle to prevent the bag on the support from being double counted.

The preferred embodiment of the invention is shown in FIGS. 1 and 2. FIG. 1 shows the inventive system 10, while FIG. 2 shows one of the supports of system 10 with a bag hanging on it. System 10 comprises a structure 20. In this example, structure 20 is coupled to the underside 14 of rack 12 that is used to hold a box that contains multiple empty sponge counter bags. Rack 12 is available from bag manufacturers. In this example, structure 20 is coupled directly to rack 12, however that is not a limitation of the invention as structure 20 or another structure within the scope of the invention can be a stand-alone structure, or can be coupled to another structure that is located in an operating room. Structure 20 includes a number of supports, each of which is designed to hold a single sponge counting bag. In this example, there are five supports 31-35, although the quantity of supports is not a limitation of the invention. Each support has two hooks or other structures that are designed to grasp or hold in some manner a single sponge counter bag. In this example, bag 50 defines ten pockets such as pocket 52, with a sponge 54 shown in pocket 52; for lap pads and squares the bag typically comprises five pockets. The invention can be used with any type of sponge counter bag and a bag that has one or more pockets. Typically, these bags are entirely clear, or at least the front panel of the bag is clear so that the sponges that are located in the bag are easily visible and can be quickly counted. In this example, two hooks 41 and 42 are attached to support 31 and spaced appropriately so that they fit through the holes at the top of bag 50, as shown in FIG. 2. Other structures can be used to support bags such as clamps or other mechanical devices.

In use, structure 20 can hold up to five bags. The bags hang down from the supports and partially overlap one another. The supports are constructed so that they can be rotated (typically through 180°) to facilitate counting of the sponges. In this embodiment, the rotation is accomplished with a central spindle 22 and a sleeve (five sleeves numbered 23-27) located over the spindle and each carrying one support. The construction can be of metal or plastic or other materials acceptable to operating room standards, with metal being the currently preferred medium. The sleeves can rotate about spindle 22, and since they carry the support bars, the sleeves facilitate rotation of the support bars about spindle 22. In this example, structural members or bars 44 and 45 located spaced from and parallel to spindle 22 are present to provide stop positions for the rotational motion of the supports. This construction prevents a support from being rotated through 360°, which could cause confusion in use. Lower bar 43 supports the ends of bars 44 and 45. Bar 43 can be coupled to spindle 22.

In use, bags are placed on the hooks of the supports, beginning with support 35. As one bag is filled, another bag can be added. When it is time to count the sponges, the sponges in the outermost bag are counted and then the support from which this bag is supported is rotated through 180° to expose the next bag. This construction allows a simple flipping motion to move a bag from the "yet to be counted" to the "already counted" category. Also, many bags have an opaque backing. Once the supports are flipped to the "already counted" position, this opaque back will face forward and thus serve as an indication that the bag has been counted.

The invention allows multiple bags to be held hands-free, and facilitates the task of accurately counting the sponges located in the bags.

While it will be apparent that the illustrated embodiments of the invention herein disclosed are calculated adequately to fulfill the object and advantages primarily stated, it is to be understood that the invention is susceptible to variation, modification, and change within the spirit and scope of the subjoined claims. It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desire to secure by Letters Patent is:

What I claim as my invention is:

1. A rack for surgical sponge counter bags that facilitates sponge counting, comprising:
    a spindle;
    a plurality of rotatable support members mounted for rotation about the spindle, each support member carrying one or more mechanical devices that are constructed and adapted to grasp a sponge counter bag;
    a frame having two spaced bars, wherein the spindle is attached to the frame between and parallel with the two spaced bars such that the two spaced bars act as positional stops to prevent the rotatable support members from rotating through more than 180 degrees;
    one or more surgical sponges; and
    at least one surgical sponge counter bag that is grasped by the mechanical device of one of the support members, and has a pocket that holds the surgical sponge, the bag being constructed so that, if the sponge is in the pocket, the sponge in the pocket is visible from outside the pocket.

2. A method for counting surgical sponges recovered from a surgery, and employing a rack for surgical sponge counter bags that facilitates sponge counting, comprising:
    a spindle;
    a plurality of rotatable support members mounted for rotation about the spindle, each support member carrying one or more mechanical devices that are constructed and adapted to grasp a sponge counter bag;
    a frame having two spaced bars, wherein the spindle is attached to the frame between and parallel with the two spaced bars such that the two spaced bars act as positional stops to prevent the rotatable support members from rotating through more than 180 degrees;
    one or more surgical sponges recovered from a surgery; and
    a first and a second surgical sponge counter bags that can be grasped by the mechanical devices of a first and a second support members of the plurality of support members respectively, and have a pocket that could hold a surgical sponge, the bags being constructed so that, if the sponge is in the pocket, the sponge in the pocket is visible from outside the pocket, comprising the steps of;
    a.) positioning all of the support members against one of the bars in a first position so that they all extend in a first direction from the spindle;
    b.) mounting the first surgical sponge counter bag on one of the support members:
    c.) recovering a surgical sponge from a surgery;
    d.) placing the surgical sponge in a pocket of the first surgical sponge counter bag;
    e.) when all of the pockets on the first surgical sponge counter bag contain a sponge, install the second search surgical sponge counter bag on the second support member,
    f.) continued to insert recovered surgical sponges into the second surgical sponge counter bag;
    g.) when it appears that there will be no further sponges recovered from surgery, counting the surgical sponges in the first surgical sponge counter bag,
    h.) when the counting of the surgical sponges in the first surgical sponge bag is complete, moving the support member that grasps the first surgical sponge counter bag to the other one of the bars to a second position diametrically opposed from the first position, to indicate that the sponges in the first surgical sponge counter bag have been counted; and
    i.) counting the surgical sponges in the second surgical sponge counter bag.

* * * * *